(12) United States Patent
Caudle et al.

(10) Patent No.: US 7,108,691 B2
(45) Date of Patent: Sep. 19, 2006

(54) FLEXIBLE SCANNING BEAM IMAGING SYSTEM

(75) Inventors: George Caudle, Bonne Terre, MO (US); Vladimir Lemberg, Redwood City, CA (US)

(73) Assignee: VISX, Inc., Santa Clara, CA (US)

( * ) Notice: Subject to any disclaimer, the term of this patent is extended or adjusted under 35 U.S.C. 154(b) by 122 days.

(21) Appl. No.: 10/367,015

(22) Filed: Feb. 12, 2003
(Under 37 CFR 1.47)

(65) Prior Publication Data

US 2004/0073200 A1    Apr. 15, 2004

Related U.S. Application Data

(60) Provisional application No. 60/356,840, filed on Feb. 12, 2002.

(51) Int. Cl.
*A61B 18/18* (2006.01)

(52) U.S. Cl. .............................. 606/10; 606/4; 351/208

(58) Field of Classification Search .................... 606/4, 606/5, 10–12, 17, 18; 351/208–212
See application file for complete search history.

(56) References Cited

U.S. PATENT DOCUMENTS

| | | | |
|---|---|---|---|
| 4,170,398 A * | 10/1979 | Koester | 359/219 |
| 4,257,687 A * | 3/1981 | Kohayakawa | 351/208 |
| 4,397,310 A | 8/1983 | Pomerantzeff | |
| 4,544,246 A | 10/1985 | Crane et al. | |
| 4,588,270 A * | 5/1986 | Tamaki | 351/212 |
| 4,628,416 A | 12/1986 | Dewey | |
| 4,881,808 A * | 11/1989 | Bille et al. | 351/221 |
| 4,887,592 A | 12/1989 | Loertscher | |
| 4,901,718 A * | 2/1990 | Bille et al. | 606/4 |
| 4,941,093 A | 7/1990 | Marshall et al. | |
| 5,171,242 A | 12/1992 | Dewey et al. | |
| 5,284,477 A | 2/1994 | Hanna et al. | |
| 5,490,849 A | 2/1996 | Smith | |
| 5,618,285 A | 4/1997 | Zair | |
| 5,634,923 A | 6/1997 | Brenner et al. | |
| 5,777,719 A * | 7/1998 | Williams et al. | 351/212 |
| 5,783,798 A | 7/1998 | Abraham | |
| 5,928,221 A | 7/1999 | Sasnett et al. | |
| 6,004,313 A | 12/1999 | Shimmick et al. | |
| 6,159,202 A | 12/2000 | Sumiya et al. | |
| 6,325,512 B1 * | 12/2001 | Wei | 351/209 |

* cited by examiner

*Primary Examiner*—A. Farah
(74) *Attorney, Agent, or Firm*—Townsend and Townsend and Crew LLP (57) ABSTRACT

The present invention is directed to a flexible scanning beam imaging system. In specific embodiments, the scanning beam imaging system comprises a mask, and an objective lens having an objective lens focal point disposed between the mask and the objective lens. A field lens device is disposed before the mask to direct a light beam through the mask and focus the light beam at a field lens focal point. The field lens focal point is located between the field lens and the objective lens. One or more scanning mirrors are disposed at or near the objective lens focal point. As a result, the beam will be directed to different locations across the objective lens by the scanning mirror(s), and will travel from the objective lens substantially collimated and parallel toward a surface illuminated by the beam. This substantially collimated and parallel beam provides a large depth of field of the ablation pattern.

61 Claims, 6 Drawing Sheets

FLEXIBLE SCANNING BEAM IMAGING SYSTEM

CROSS-REFERENCES TO RELATED APPLICATIONS.

This application claims benefit to provisional patent application No. 60/356,840, filed on Feb. 12, 2002, the disclosure of which is incorporated herein by reference.

BACKGROUND OF THE INVENTION

The present invention relates generally to light beam scanning and imaging systems and methods, and more particularly to a system and a method for ablating a desired shape in a material with a scanning laser beam.

A laser beam imaging system for performing laser ablation generally includes a mask or aperture which is imaged onto the target, typically by an objective lens. For laser eye surgery, the target is the corneal tissue. A field lens may be placed before the mask to alter the characteristics such as the shape of the laser beam at the objective lens in order to reduce the aberration or distortion of the image caused by the objective lens. For example, the laser beam may be partially focused to reduce the diameter of the beam at the objective lens, which in turn will reduce certain types of distortion in the image. The field lens may also be used to focus the laser beam at the focal point of the objective lens to produce an approximately collimated beam emerging from the objective lens onto the target, which can increase the depth of field of the image. To produce a scanning beam, a scanning system is typically placed at or distal of the objective lens. These techniques are typically sensitive to errors in positioning the target along the laser beam path. This sensitivity to positioning errors can produce deviations in the position, size and energy/intensity of a light beam striking a target.

In light of the above, improved systems and methods for delivering a light beam to a target are desirable.

BRIEF SUMMARY OF THE INVENTION

The present invention is directed to a flexible system for scanning and imaging a beam of light. In specific embodiments, one or more scanning mirrors are placed between the mask and the objective lens, at or near the focal point of the objective lens. As a result, the beam will be directed to different locations across the objective lens by the scanning mirror(s), and will travel from the objective lens substantially parallel to the optical axis of the scanning beam imaging system. This parallel beam provides a large depth of field of the ablation pattern. A field lens device brings the beam to a focus between the field lens and the objective lens to produce a substantially collimated beam after the objective lens. This substantially collimated beam also provides a large depth of field of the ablation pattern. The field lens device may include a Galilean telescope, a multi element zoom lens or a single optical element. The beam is focused in a manner that avoids damaging the scanning mirror(s), and allows the fluence on the scanning mirrors and other optical elements to be kept at a low level.

The system has several advantages over previous systems. For instance, the scanned beam pattern is substantially collimated and parallel between the objective lens and the target. The beam intensity and size at the mask can be easily varied by changing the position of the lenses of the Galilean telescope. This beam variation can be done while keeping the position of the focused beam at nearly the same location, and thus keep the beam intensity nearly the same on the subsequent optical elements in the path of the beam. The beam has a substantially similar shape at the mask as the beam size is varied by changing the position of the lenses of the Galilean telescope. The size of the beam can be varied without an excessive increase in the beam intensity on the subsequent optical elements. The relative intensity of the laser beam on a surface of the target will be substantially the same as it is in the plane of the mask. A beam which has a uniform intensity over an aperture formed in a mask will have a uniform intensity over the image of the aperture at the target. The system is especially suited for ablating various shapes with a scanning pulsed laser. It permits the beam shape to be optimized with the telescope and the mask.

In accordance with an aspect of the present invention, a system for scanning a light beam over a target comprises a first lens element disposed along the path of the light beam. The first lens element focuses the laser beam to form a focused beam along the beam path at a beam focal point. A second lens element is disposed along the path of the light beam. The second lens element substantially collimates the beam of light, and the beam focal point is disposed between the first lens element and the second lens element. A first movable mirror scans the light beam from a first position on the target to a second position on the target. The mirror has a surface intersecting the beam at a position along the beam path between the first lens element and the second lens element. The path of the collimated light beam in the first position on the target is substantially parallel to the path of the collimated light beam in the second position on the target.

In specific embodiments, the position of the beam focal point is separated from the position of the surface of the mirror. A dimension across the surface of the mirror intersecting the beam is greater than about 10% of a width of the beam at the second lens element. Preferably, a dimension across the surface of the mirror intersecting the beam is greater than about 25% of a width of the beam at the second lens element. More preferably, a dimension across the surface of the mirror intersecting the beam is greater than about 50% of a width of the beam at the second lens element. A full angle of the substantially collimated light beam is less than about 15 milliradians, and the path of the beam in the first position on the target is parallel to the path of the beam in the second position on the target to within about 15 milliradians. An aperture is disposed along the path of the laser beam, and the second lens element forms an image of the aperture near the target. The lens elements are selected from the group consisting of reflecting, refracting and diffracting lens elements. The first lens element is a field lens device comprising a plurality of lenses. The plurality of lenses are movable to adjust at least one of the size and the intensity of the beam without substantially moving the beam focal point. The field lens device comprises a Galilean telescope. The second lens element is an objective lens having an objective lens focal point disposed along the laser beam path. A second movable mirror scans the light beam from the first position on the target surface to the second position on the target surface with a movement of the second mirror. The second mirror is disposed along the beam path between the field lens and the objective lens. The first mirror and the second mirror are disposed on opposite sides of the objective lens focal point along the beam path. The distance between the first mirror and the second mirror is less than the focal length of the objective lens. Preferably, the distance between the mirrors is less than about 20% of the focal length of the objective lens. More preferably, the distance between the mirrors is less than about 10% of the focal length of the objective lens.

In accordance with another aspect of the present invention a system for ablating a surface of a material with a light beam forms a predetermined shape in the material. A light source makes a beam of an ablative light energy and the beam travels along a path. A first movable mirror scans a substantially collimated and parallel light beam from a first position on the surface to a second position on the surface. A processor is coupled to the mirror and the light source. The processor comprises a set of machine readable instructions adapted to ablate the material with the beam to form the predetermined shape in the material.

In accordance with a further aspect of the present invention a method for delivering a light beam to a target includes directing the light beam along a path to a first lens element. The first lens element focuses the beam to form a focused beam along the beam path at a beam focal point. The focused beam is directed to a second lens element that forms a substantially collimated light beam along the beam path near the target. The beam focal point is positioned between the first lens element and the second lens element. Moving a first mirror scans the light beam from a first position on the target to a second position on the target. The mirror has a surface positioned along the beam path. The mirror surface is between the first lens element and second lens element. The path of the collimated light beam in the first position on the target is substantially parallel to the path of the collimated light beam in the second position on the target. The light beam may pass through an aperture and form an image of the aperture near the target. The lens elements may be selected from the group consisting of reflecting, refracting and diffracting lens elements.

In accordance with another aspect of the invention a method of ablating a surface of a material with a light beam to form a predetermined shape in the material includes generating a beam of an ablative light energy. The beam travels along a path. The beam is directed to a first lens element that focuses the beam to form a focused beam along the path. The focused beam forms at a beam focal point. The focused beam is directed to a second lens element that substantially collimates the light beam along the beam path near the surface. The material is ablated with the beam to form the predetermined shape in the material.

DETAILED DESCRIPTION OF THE INVENTION

Figure 1:
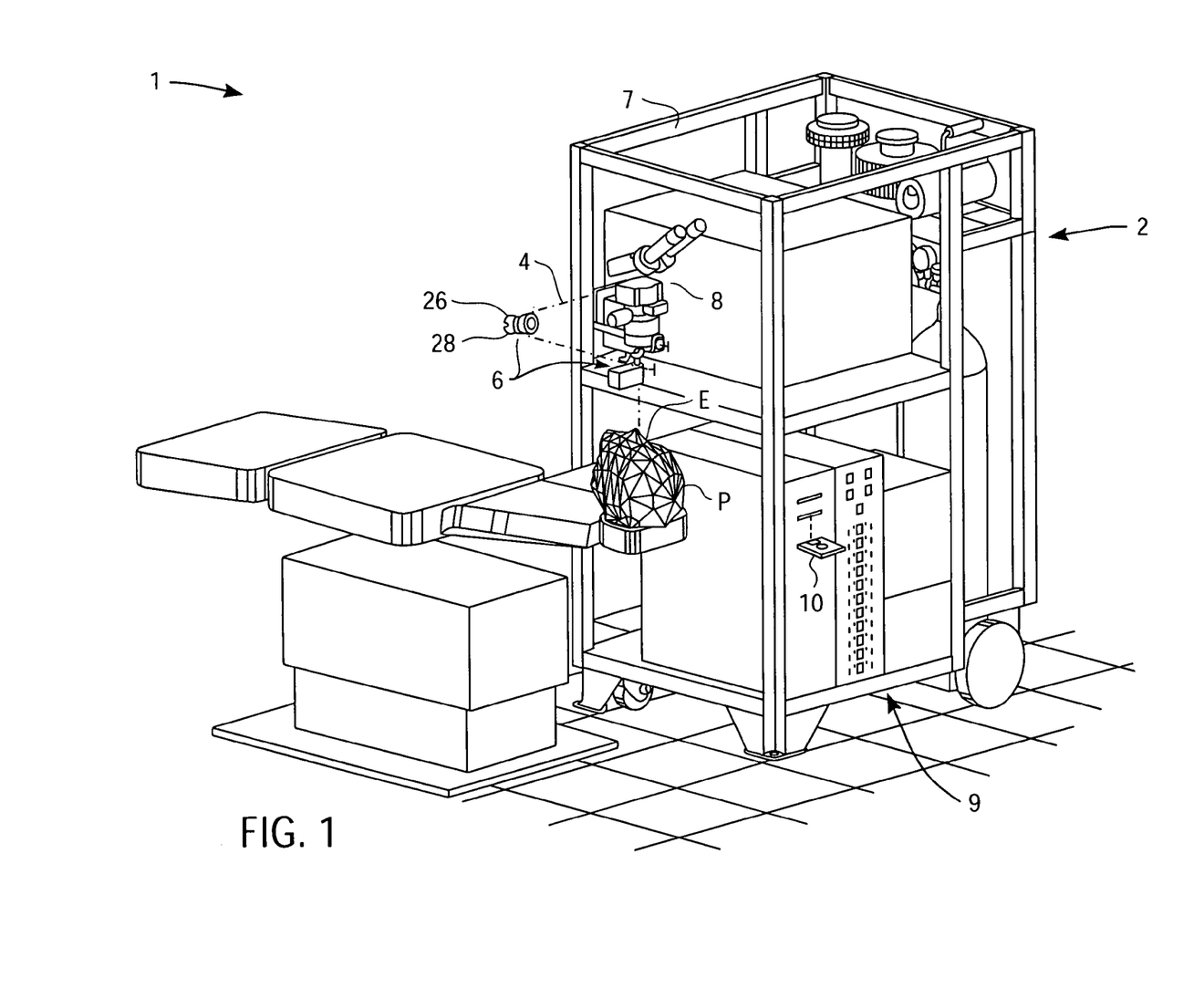
FIG. 1 is a perspective view of a laser eye surgery system for incorporating an embodiment of the present invention.

Referring now to FIG. 1, a laser eye surgery system 1 for incorporating the present invention includes a laser 2 that produces a laser beam 4. Laser 2 is optically coupled to laser beam delivery optics 6, which direct laser beam 4 to an eye E of patient P. A delivery optics support structure (not shown here for clarity) extends from a frame 7 supporting laser 2. A microscope 8 is mounted on the delivery optics support structure, the microscope often being used to observe a cornea of eye E.

The laser beam scanning system of the present invention is particularly suited for ablating various shapes with a scanning pulsed laser. It permits the beam shape to be optimized with a Galilean telescope and mask. The system provides a large depth of field of the ablation pattern, and allows the fluence on the scanning mirrors 26, 28 and other optical elements to be kept at a relatively low level. As used herein, an illumination surface encompasses an intended position of a surface of an object illuminated by the laser beam, such as a laser treatment plane where an ablation is formed in a calibration material and a corneal treatment surface where a cornea is ablated.

Laser 2 generally comprises an excimer laser, ideally comprising an argon-fluorine laser producing pulses of laser light having a wavelength of approximately 193 nm. Laser 2 will preferably be designed to provide a feedback stabilized fluence at the patient's eye, delivered via delivery optics 6. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 215 nm and/or those which utilize frequency-multiplying techniques. In alternate embodiments, the laser beam source employs a solid state laser source having a wavelength between 193 and 215 nm as described in U.S. Pat. Nos. 5,520,679, and 5,144,630 to Lin and U.S. Pat. No. 5,742,626 to Mead, the full disclosures of which are incorporated herein by reference. In another embodiment, the laser source is an infrared laser as described in U.S. Pat. Nos. 5,782,822 and 6,090,102 to Telfair. Hence, although an excimer laser is the illustrative source of an ablating beam, other lasers may be used in the present invention.

Laser 2 and delivery optics 6 will generally direct laser beam 4 to the eye E of patient P under the direction of a computer 9. Computer 9 will generally selectively adjust laser beam 4 to expose portions of the cornea to the pulses of laser energy so as to effect a predetermined sculpting of the cornea and alter the refractive characteristics of the eye. In many embodiments, both laser 4 and the laser beam delivery optical system 6 will be under computer control of processor 9 to effect the desired laser sculpting process.

Laser beam 4 may be adjusted to produce the desired sculpting using a variety of alternative mechanisms. The laser beam 4 may optionally be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size of the laser spot as described above.

Typically, system 1 will scan the laser beam over the surface of the eye E using mirrors 26, 28 (of FIG. 1), and will often control the number of pulses and/or dwell time at each location, as described, for example, in U.S. Pat. No. 4,665,913 (the full disclosure of which is incorporated herein by reference). Some embodiments may have scanning components similar to those of other scanning laser systems such as the LSX laser by LaserSight, LadarVision by Alcon/Autonomous, and the 217C by Technolas. The computer programs and control methodology for scanned laser pattern tailoring techniques are well described in the patent literature.

Additional components and subsystems may be included with laser system 1, as should be understood by those of skill in the art. For example, spatial and/or temporal integrators may be included to control the distribution of energy within the laser beam, as described in U.S. Pat. Nos. 5,646,791 and 5,912,775 to Glockler, the full disclosure of which are incorporated herein by reference. An ablation effluent evacuator/filter, and other ancillary components of the laser surgery system which are not necessary to an understanding of the invention, need not be described in detail for an understanding of the present invention.

As mentioned above, laser system 1 will generally include a computer or programmable processor 9. Processor 9 may comprise (or interface with) a conventional PC system including the standard user interface devices such as a keyboard, a display monitor, and the like. Processor 9 will typically include an input device such as a magnetic or optical disk drive, an internet connection, or the like. Such input devices will often be used to download a computer executable code from a tangible storage media embodying any of the methods of the present invention. Tangible storage media 10 may take the form of a floppy disk, an optical disk, a data tape, or the like, and the processor 9 will include the memory boards and other standard components of modern computer systems for storing and executing this code.

Figure 2:
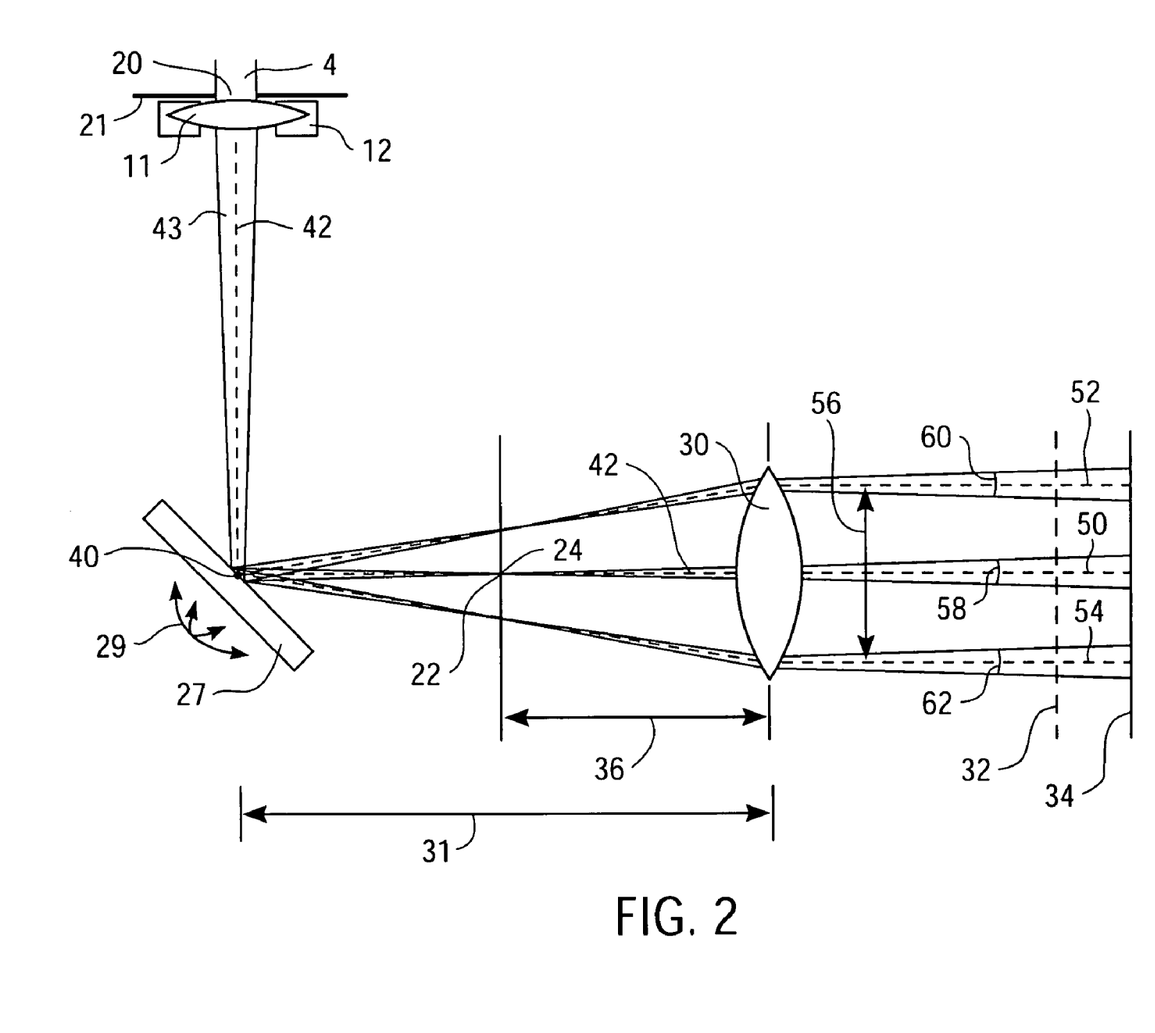
FIG. 2 is a simplified diagram according to an embodiment of the invention schematically illustrating an optical system employing an aperture, a field lens, an objective lens and a movable mirror that scans a collimated and parallel laser beam over a surface.

An embodiment of the invention is schematically illustrated in FIG. 2. A laser beam 4 passes through an aperture 20 formed in mask 21. A field lens device 12 comprises a first lens element 11 positioned near aperture 20. The laser beam 4 travels along a path 43 which is typically coincident with optical axis 42. The laser beam 4 is directed to a movable mirror 27 that is positioned along the laser beam path. The mirror 27 is mounted on a gimbal, and the laser beam 4 reflects off a surface of the mirror 27. The gimbal is capable of rotational movement under computer control as indicated by arrows 29. The laser beam focuses to a waist at laser beam focal point 24. Laser beam focal point 24 is typically coincident with a position of a field lens focal point 22. However, in alternate embodiments, laser beam 4 is slightly converging or diverging as it passes through lens 14 and causes the laser beam focal point 24 to be at a slightly different position than field lens focal point 22.

The mirror 27 pivots about an objective lens focal point 40. Rotational movement of mirror 27 deflects the laser beam path. Deflected laser beam paths are schematically illustrated at 52 and 54. An objective lens 30 comprises a second lens element that forms an image of aperture 20 at image plane 32.

In other embodiments, the objective lens 30 comprises several lens elements. Image plane 32 is near illumination surface 34. In another embodiment, image plane 32 and illumination surface 34 are positioned in substantially the same place. The objective lens 30 is separated by a distance 31 from the mirror 27. The separation distance 31 matches the focal length of the lens 30. The beam focal point 24 is separated from objective lens 30 by a distance 36. The laser beam paths 50, 52 and 54 are substantially parallel near the illumination surface 34. As used herein substantially parallel laser beam paths encompass laser beam paths that are parallel to within about 30 milliradians. Preferably, the laser beam paths are parallel to within 15 milliradians as the beam scans over illumination surface 34. More preferably, the laser beam paths are parallel to within 10 milliradians as the beam scans over illumination surface 34.

Distance 36 need not match the focal length of the objective lens 30, as shown, and the laser beam paths 50, 52, and 54 can diverge with a slight angles 58, 60 and 62. Although the laser beam paths 50, 52 and 54 diverge with slight full angles 58, 60 and 62 respectively, the laser beam paths are substantially collimated near illumination surface 34. As used herein, a substantially collimated laser beam path encompasses a laser beam path that is collimated to within about 30 milliradians or less for the full width of the beam. Preferably, the laser beam path is collimated to within 15 milliradians. More preferably, the laser beam path is collimated to within 10 milliradians. In alternate embodiments, the position of the scanning mirror 27 and laser beam focal point 24 vary relative to the objective lens focal point 40, and these embodiments achieve a substantially collimated and parallel scanning laser beam. In other embodiments, the aperture 20 formed in mask 21 maybe positioned to form an image of mask 21 near field lens 11. The image of mask 21 formed near field lens 11 is imaged by objective lens 30 to form an image of mask 21 at image plane 32 near illumination surface 34.

Figure 3:
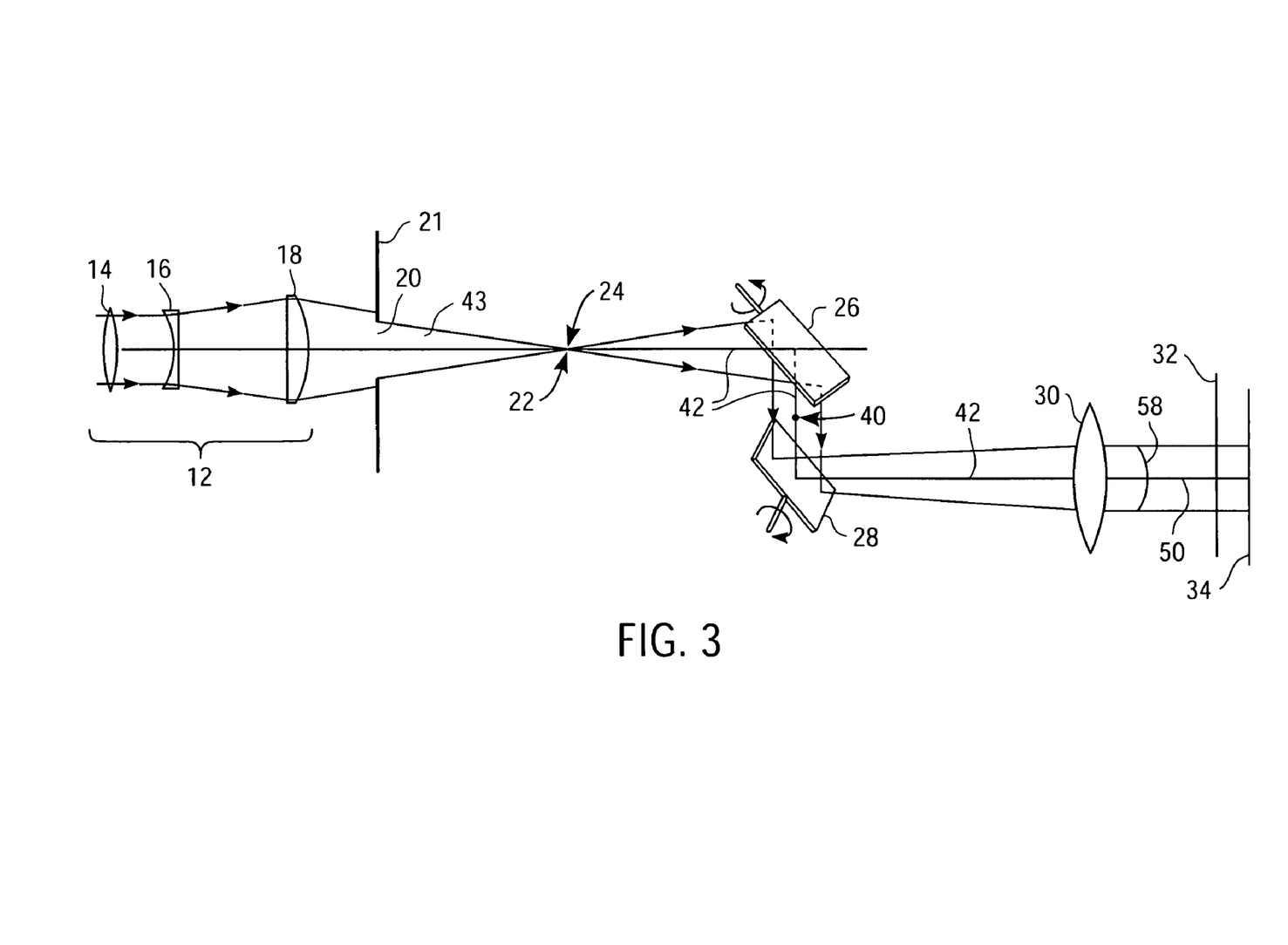
FIG. 3 is a simplified diagram according to another embodiment of the invention schematically illustrating an optical system that includes an aperture, a variable field lens device, an objective lens and movable mirrors.

In a preferred embodiment shown in FIG. 3, the laser beam delivery system includes a field lens device 12 placed before an aperture 20 formed in mask 21. The field lens device 12 comprises lens elements 14, 16 and 18. The field lens device 12 directs the beam through the aperture 20 and focuses the beam to a waist at a laser beam focal point 24 that preferably coincides with the location of the field lens focal point 22. After traveling past the beam focal point 24, the beam is reflected by a pair of surfaces on a pair of scanning mirrors 26, 28. After reflecting from the surfaces of the mirrors the light beam reaches an objective lens 30 that comprises a single lens element. In alternate embodiments, the objective lens 30 comprises a plurality of lens elements. The objective lens 30 forms an image of the aperture 20 at the image plane 32.

In an alternate embodiment, an aperture is not imaged at an image plane 32. The position of the beam focal point 24 relative to the objective lens 30 is controlled to produce a beam having a desired width and collimation at illumination surface 34. As an example, the laser beam focal point 24 is located between objective lens 30 and objective lens focal point 40.

In some embodiments, a field lens device 12 having multiple lenses is used. In the specific embodiment shown in FIG. 3, for example, the field lens device 12 comprises lens elements 14, 16 and 18. Lenses 16 (diverging) and 18 (converging) form a Galilean telescope that is disposed behind the lens 14 and receives the converging light beam from the lens 14. In an alternate embodiment of the field lens device 12, the Galilean telescope is positioned before lens 14 along the laser beam path, and the lens 14 receives the light beam after the Galilean telescope. In a further embodiment, the positions of the lenses of the Galilean telescope are inverted along the laser beam path to decrease a width of the laser beam. In other embodiments, the aperture is positioned near other lenses of the field lens device 12, for example, near lens 14. An alternate embodiment employs a zoom lens having several lens elements as a field lens device 12. Referring again to the embodiment of FIG. 3, the field lens device 12 brings the beam to a focus at the laser beam focal point 24 which is located between the aperture 20 and a focal point 40 of the objective lens 30. The laser beam focal point 24 preferably coincides with the field lens focal point 22. However, the laser beam focal point 24 does not coincide with the locations of the surfaces of scanning mirrors 26, 28 to keep the fluence on the scanning mirrors 26, 28 at a relatively low level and avoid damaging the mirrors 26, 28. A dimension across the surface of the mirror 26 intersecting the path 43 of beam 4 is typically greater than about 10% of a width of the beam at the second lens element 30. Preferably, a dimension across the surface of the mirror 26 intersecting the path 43 of beam 4 is greater than about 25% of a width of the beam at the second lens element 30. More preferably a dimension across the surface of the mirror 26 intersecting the path 43 of beam 4 is greater than about 50% of a width of the beam at the second lens element 30. The beam intensity and size at the aperture 20 can be easily varied by adjusting the positions of the lenses 16, 18 of the Galilean telescope. This adjustment can be accomplished while keeping the field lens focal point 22 and laser beam focal point 24 at nearly the same location, thereby keeping the beam intensity relatively low on the subsequent optical elements in the path of the beam. Because the beam size is varied by changing the positions of the lenses 16, 18 of the Galilean telescope, the beam has a similar shape at the aperture 20.

For the scanning system, it is desirable to produce as much depth of field at the image plane 32 as possible. It is also desirable to avoid changes in beam characteristics and to provide continuance to the laser beam characteristics as a surface of an illuminated object moves along the laser beam path relative to illumination surface 34. Such motion can occur during laser eye surgery. This continuance is accomplished by substantially collimating the focused beam with the objective lens 30. The collimation is sufficient to maintain a desired depth of field at the image plane 32, and to maintain the characteristics of the laser beam near the illumination surface 34. As shown in FIG. 3, the image plane does not necessarily coincide with the illumination surface 34, and the illumination surface 34 is beyond the depth of field of the image of the aperture formed at image plane 32.

In the embodiment shown in FIG. 3, the scanning mirrors 26, 28 are placed near the focal point 40 of the objective lens 30, and are symmetrically disposed on opposite sides of the focal point 40 along the optical axis 42. The spacing between the scanning mirrors 26, 28 is small compared to the focal length of the objective lens 30 which is the distance between the focal point 40 and the objective lens 30. For instance, the spacing is typically less than about 20%, and more desirably less than about 10%, of the focal length of the objective lens 30. In a specific example, the focal length of the object lens 30 is about 20 cm, and the spacing between the scanning mirrors 26, 28 is about 1 cm.

Figure 3A:
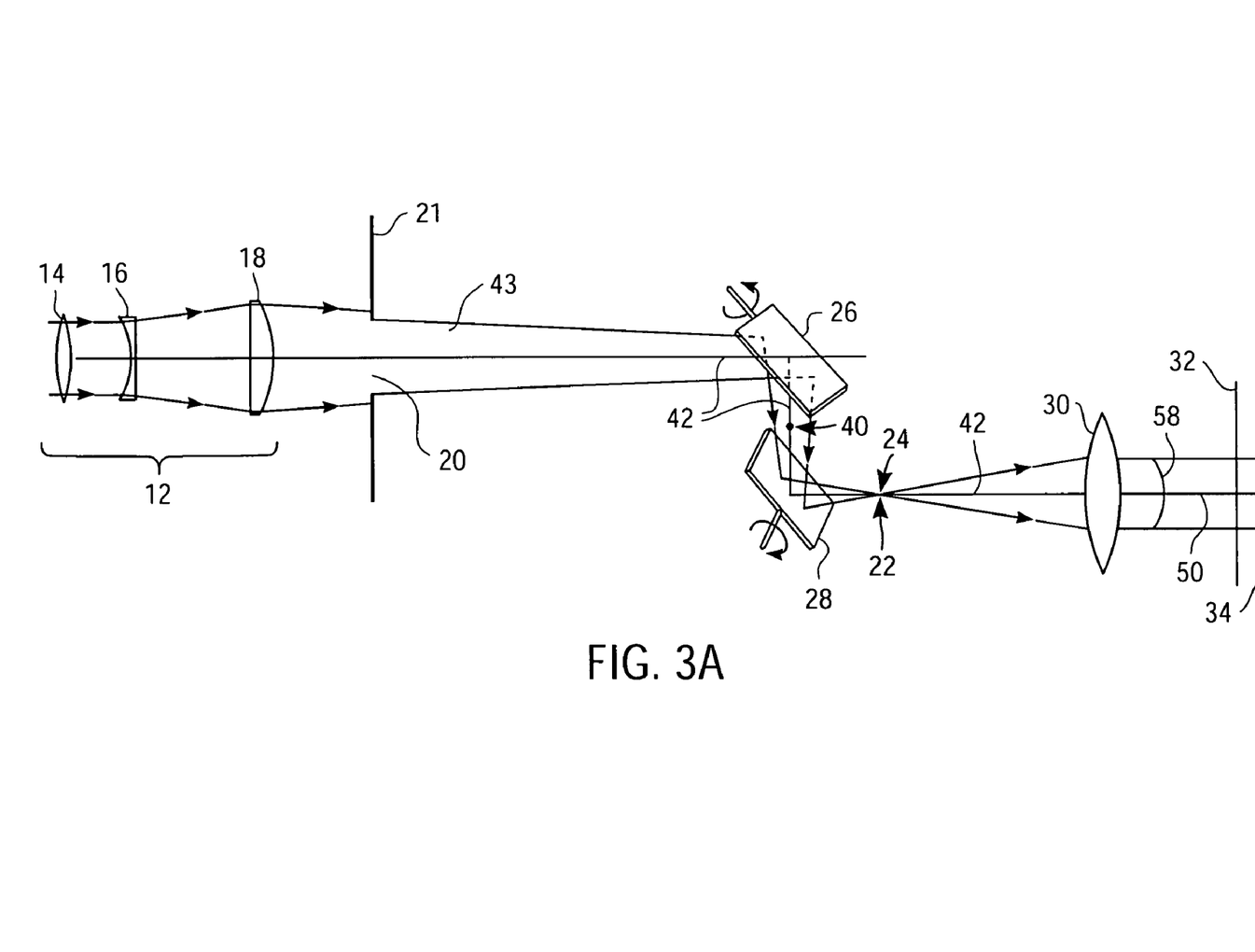
FIG. 3A is a simplified diagram according to another embodiment of the invention schematically illustrating a focal point of a field lens disposed between the focal point of the objective lens and the objective lens.

By positioning the scanning mirrors 26 and 28 near the objective lens focal point 40, the paths of the laser beam scanning over the illumination surface are substantially parallel as described above. The pair of scanning mirrors 26, 28 are disposed near the objective lens focal point 40. Such a configuration has the property that the path of the beam which is directed to different locations on the objective lens 30 by the scanning mirrors 26, 28 will travel from the objective lens 30 substantially parallel to the optical axis of the system. As a result, the laser beam paths are substantially parallel as the laser beam scans over the illumination surface 34 and image plane 32. The individual laser beam paths need not be absolutely collimated and parallel to within a few seconds of arc to enable the present invention. A substantial degree of beam path collimation, and a substantial degree of parallelism among scanned beam paths produces a substantial improvement in beam shape and ablation profile as an actual position of an illuminated surface deviates from the intended illumination surface 34. As an example, an ablation profile intended to be −4 Diopters of ablated optical power in a corneal surface at the intended illumination surface 34 will remain within a desired ablation accuracy tolerance of about a quarter diopter, even if the actual position of the surface illuminated with the beam is several millimeters from the intended position In an alternate embodiment illustrated in FIG. 3A, the beam focal point 24 is located between the objective lens focal point 40 and the objective lens. This embodiment provides a substantially collimated and parallel beam path as described above. A dimension across a path 43 of beam 4 intersecting the surface of the mirror 28 is typically greater than about 10% of a width of the beam at the second lens element.

Figure 4:
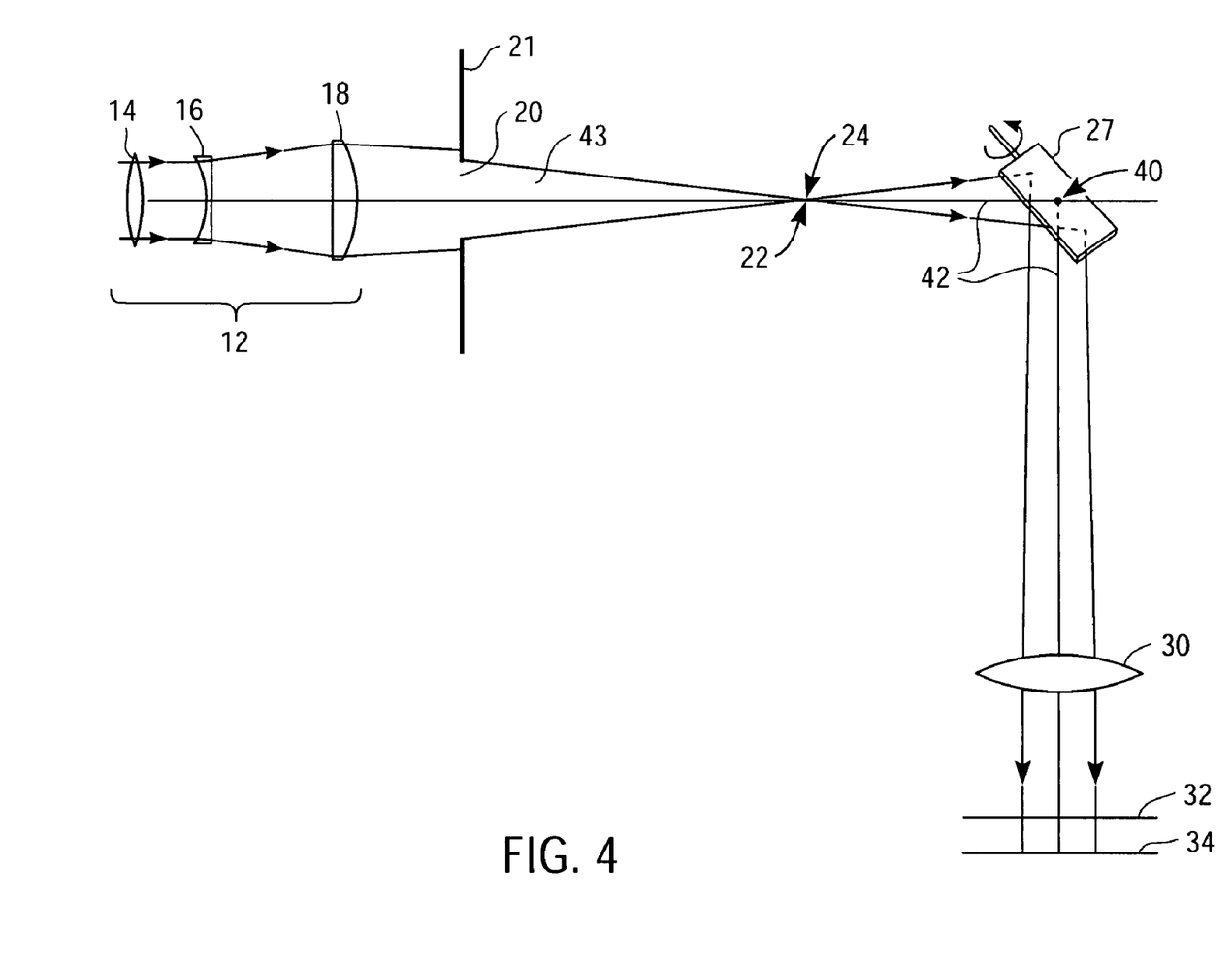
FIG. 4 is a simplified diagram according to a further embodiment of the invention schematically illustrating an optical system that includes an aperture, variable field lens device, an objective lens and a movable mirror.

In another alternate embodiment illustrated in FIG. 4, a laser beam imaging system employs a single scanning mirror 27, in place of the pair of scanning mirrors 26, 28 of FIG. 3. The scanning mirror 27 is located at or near the focal point 40 of the objective lens 30.

Figure 5:
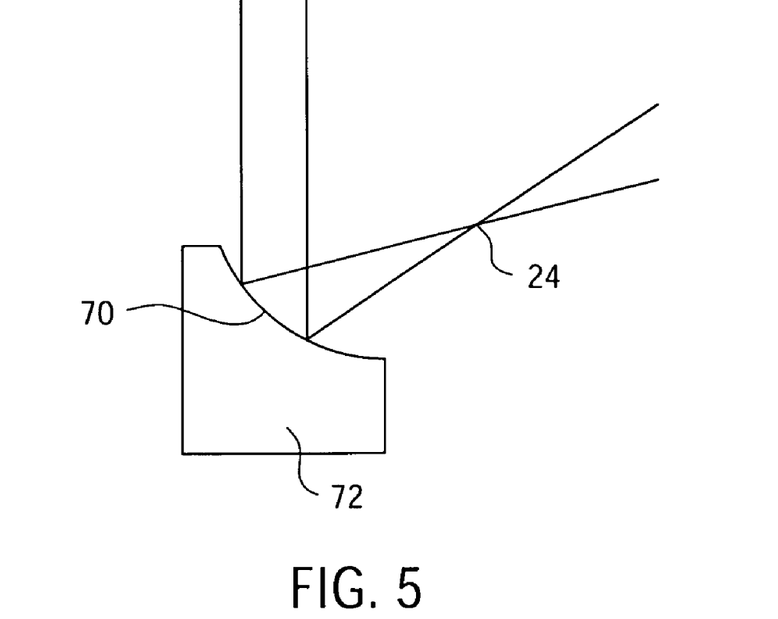
FIG. 5 is a simplified diagram according to a further embodiment of the invention schematically illustrating a mirror as a lens element.
Figure 6:
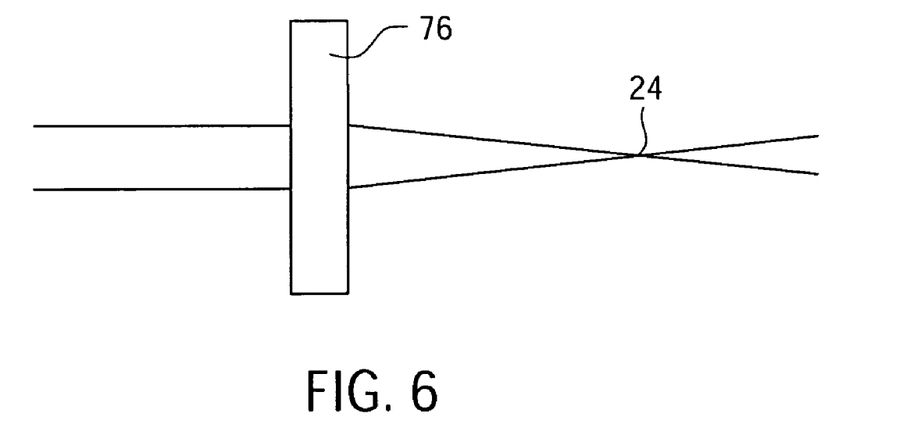
FIG. 6 is a simplified diagram according to a further embodiment of the invention schematically illustrating a diffractive optic as a lens element.

An alternate embodiment employing a reflecting curved surface 70 of a mirror 72 as a lens element to focus a light beam is illustrated in FIG. 5. Another embodiment employs a diffractive optic 76 as a lens element as shown in FIG. 6. In other embodiments a movable prism comprising an internally reflecting surface can be used as movable mirror to scan the beam as described above.

While the above provides a full and complete disclosure of the preferred embodiments of the invention, various modifications, alternate constructions and equivalents may be employed as desired. For example, a scanning system can be constructed with reflective and diffractive lens elements. Also, laser beam integration techniques can be used in conjunction with the scanning system. Moreover, different scanning mirror arrangements may be used. Any suitable scanning scheme may be adapted to the present system. Therefore, the above description and illustrations should not be construed as limiting the invention, which is defined by the appended claims.

What is claimed is:

1. A system for scanning a light beam over a target, the system comprising:
   a first lens element disposed along a path of the light beam, the first lens element forming a converging light beam along the path, the converging beam forming a beam focal point beyond which the light beam becomes a diverging light beam;
   a second lens element disposed along the path of the light beam, the second lens substantially collimating the diverging light beam, the beam focal point being disposed between the first lens element and the second lens element, the second lens having a focal point disposed between the beam focal point and the first lens element; and a first movable mirror for scanning the path of the light beam from a first position on the target to a second position on the target, the mirror having a surface intersecting the beam at a position along the beam path between the first lens element and the second lens element, the path of the collimated light beam from the second lens element in the first position on the target being substantially parallel to the path of the collimated light beam from the second lens element in the second position on the target to within about 30 milliradians or less.

2. The system of claim 1 wherein a position of the beam focal point is separated from the position of the surface of the mirror.

3. The system of claim 2 wherein a dimension across the surface of the mirror intersecting the beam is greater than about 10% of a width of the beam at the second lens element.

4. The system of claim 2 wherein a full angle of the substantially collimated light beam is less than about 15 milliradians and the path of the beam in the first position on the target is parallel to the path of the beam in the second position on the target to within about 15 milliradians.

5. The system of claim 2 further comprising an aperture disposed along the path of the beam, the second lens element forming an image of the aperture near the target.

6. The system of claim 5 wherein the lens elements are selected from the group consisting of reflecting, refracting and diffracting lens elements.

7. The system of claim 5 wherein the first lens element comprises a field lens device comprising a plurality of lenses.

8. The system of claim 7 wherein the plurality of lenses are movable to adjust at least one of the size and the intensity of the beam without substantially moving the beam focal point.

9. The system of claim 7 wherein the field lens device comprises a Galilean telescope.

10. The system of claim 5 wherein the second lens element comprises an objective lens having an objective lens focal point disposed along the beam path.

11. The system of claim 10 further comprising a second movable mirror to scan the light beam from the first position on the surface to the second position on the surface with a movement of the second mirror, the second mirror being disposed along the beam path between the field lens and the objective lens.

12. The system of claim 11 wherein the first mirror and the second mirror are disposed on opposite sides of the objective lens focal point along the beam path.

13. The system of claim 12 wherein a distance between the first mirror and the second mirror is less than a focal length of the objective lens.

14. The system of claim 13 wherein the distance between the mirrors is less than about 20% of the focal length of the objective lens.

15. The system of claim 14 wherein the distance between the mirrors is less than about 10% of the focal length of the objective lens.

16. The system of claim 1, wherein the beam focal point is disposed along the beam path between the first lens element and the mirror.

17. The system of claim 1, wherein the beam focal point is disposed along the beam path between the mirror and the second lens element.

18. The system of claim 1, wherein the substantially collimated light beam is collimated to within about 30 milliradians or less for the full width of the beam.

19. The system of claim 1, wherein the position of the second lens element is adjustable along the path of the light beam between the mirror and the target such that the distance between the second lens element and the beam focal point is greater than, less than, or equal to a second lens element focal length.

20. A system for ablating a surface of a material with a light beam to form a predetermined shape in the material, the system comprising:

a light source for making a beam of an ablative light energy, the beam traveling along a path;

a first lens element disposed along the beam path to form a converging beam along the path, the converging beam forming a beam focal point beyond which the light beam becomes a diverging light beam;

a second lens element disposed along the beam path to receive the diverging light beam and form a substantially collimated light beam along the beam path near the, surface, the focal point being disposed between the first lens element and the second lens element;

a first mirror to scan the path of the light beam from a first position on the surface to a second position on the surface with a movement of the first mirror, the first mirror having a surface intersecting the beam at a position along the beam path between the first lens element and second lens element;

a second movable mirror to scan the light beam from the first position on the surface to the second position on the surface with a movement of the second mirror, the second mirror being disposed along the beam path between the first lens element and the second lens element, the path of the collimated light beam from the second lens element in the first position on the surface being substantially parallel to the path of the collimated light beam from the second lens element in the second position on the surface to within about 30 milliradians or less; and a processor coupled to the first and second mirrors and the light source, the processor comprising a set of machine readable instructions adapted to ablate the material with the beam to form the predetermined shape in the material;

wherein the second lens element has a focal point disposed between the first mirror and the second mirror.

21. The system of claim 20 wherein a position of the beam focal point is separated from the position of the surface of the mirror.

22. The system of claim 20 wherein a full angle of the substantially collimated beam is less than about 20 milliradians and the path of the beam in the first position on the surface is parallel to a path of the beam in the second position on the surface to within about 15 milliradians.

23. The system of claim 22 wherein a dimension across the surface of the mirror intersecting the beam is greater than about 10% of a width of the beam at the second lens element.

24. The system of claim 20 further comprising an aperture disposed along the path of the beam, the second lens element forming an image of the aperture near the surface.

25. The system of claim 24 wherein the lens elements are selected from the group consisting of reflecting, refracting and diffracting lens elements.

26. The system of claim 24 wherein the first lens element comprises a field lens device comprising a plurality of lenses.

27. The system of claim 26 wherein the plurality of lenses are movable to adjust at least one of the size and the intensity of the beam without substantially moving the beam focal point.

28. The system of claim 26 wherein the field lens device comprises a Galilean telescope.

29. The system of claim 24 wherein the second lens element comprises an objective lens having an objective lens focal point disposed along the beam path.

30. The system of claim 29 wherein the light source is a pulsed ultraviolet laser having a wavelength between about 185 and 215 nm and the material is corneal material.

31. The system of claim 20 wherein a distance between the first mirror and the second mirror is less than a focal length of the second lens element.

32. The system of claim 31 wherein the distance between the mirrors is less than about 20% of the focal length of the second lens element.

33. The system of claim 31 wherein the distance between the mirrors is less than about 10% of the focal length of the second lens element.

34. The system of claim 20 wherein the focused beam, as focused by the first lens element, is directed to the second lens element.

35. A method for delivering a light beam to a target, the method comprising:
   directing the light beam along a path to a first lens element to form a converging beam along the path, the converging beam forming a beam focal point beyond which the light beam becomes a diverging light beam;
   directing the diverging light beam to a second lens element to form a substantially collimated light beam along the beam path near the target, the beam focal point being disposed between the first lens element and the second lens element, the second lens element having a focal point disposed between the beam focal point and the first lens element; and
   scanning the path of the light beam from a first position on the target to a second position on the target by moving a first mirror, the mirror having a surface at a position along the beam path between the first lens element and second lens element, the path of the collimated light beam from the second lens element in the first position on the target being substantially parallel to the path of the collimated light beam from the second lens element in the second position on the target to within about 30 milliradians or less.

36. The method of claim 35 wherein a position of the beam focal point is different from the position of the surface of the mirror.

37. The method of claim 36 wherein a dimension across the surface of the mirror intersecting the beam is greater than about 10% of a width of the beam at the second lens element.

38. The method of claim 35 wherein a full angle of the substantially collimated beam is less than about 15 milliradians and the path of the beam in the first position is parallel to a path of the beam in the second position to within about 15 milliradians.

39. The method of claim 35 further comprising passing the light beam through an aperture and forming an image of the aperture near the target.

40. The system of claim 39 wherein the lens elements are selected from the group consisting of reflecting, refracting and diffracting lens elements.

41. The method of claim 39 wherein the second lens element comprises an objective lens having an objective lens focal point disposed along the beam path.

42. The method of claim 41 wherein the step of scanning of the light beam includes moving a second mirror, the second mirror being disposed along the beam path between the first lens element and the second lens element.

43. The method of claim 42 wherein the first mirror and second mirror are disposed on opposite sides of the objective lens focal point along the beam path.

44. The method of claim 43 wherein a distance between the first mirror and second mirror is less than a focal length of the objective lens.

45. The method of claim 44 wherein the distance between the mirrors is less than about 20% of the focal length of the objective lens.

46. The method of claim 45 wherein the distance between the mirrors is less than about 10% of the focal length of the objective lens.

47. A method of ablating a surface of a material with a light beam to form a predetermined shape in the material, the method comprising:
   generating a beam of an ablative light energy, the beam traveling along a path;
   directing the beam to a first lens element to form a converging beam along the path, the converging beam forming at a beam focal point beyond which the light beam becomes a diverging light beam;
   directing the diverging light beam to a second lens element to form a substantially collimated light beam along the beam path near the surface, the beam focal point being disposed between the first lens element and the second lens element;
   scanning the path of the light beam from a first position on the surface to a second position on the surface by moving a first mirror and a second mirror, the first mirror having a surface at a position along the beam path between the first lens element and second lens element, the second mirror having a surface at a position along the beam path between the first lens element and second lens element, the path of the collimated light beam from the second lens element in the first position on the surface being substantially parallel to the path of the collimated light beam from the second lens element in the second position on the surface to within about 30 milliradians or less; and
   ablating the material with the beam to form the predetermined shape in the material;
   wherein the second lens element has a focal point disposed between the first mirror and the second mirror.

48. The method of claim 47 wherein a position of the beam focal point is different from the position of the surface of the mirror.

49. The method of claim 47 wherein a full angle of the substantially collimated beam is less than about 15 milliradians and the path of the beam in the first position on the surface is parallel to a path of the beam in the second position on the surface to within about 15 milliradians.

50. The method of claim 49 wherein a dimension across the surface of the mirror intersecting the beam is greater than about 10% of a width of the beam at the second lens element.

51. The method of claim 47 further comprising passing the light beam through an aperture and forming an image of the aperture near the surface.

52. The system of claim 51 wherein the lens elements are selected from the group consisting of reflecting, refracting and diffracting lens elements.

53. The method of claim 51 wherein the second lens element comprises an objective lens having an objective lens focal point disposed along the beam path.

54. The method of claim 53 wherein the ablative light energy has a wavelength between about 185 and 215 nm and the material is a corneal material.

55. The method of claim 47 wherein a distance between the first mirror and the second mirror is less than a focal length of the objective lens.

56. The method of claim 55 wherein the distance between the mirrors is less than about 20% of the focal length of the objective lens.

57. The method of claim 56 wherein the distance between the mirrors is less than about 10% of the focal length of the objective lens.

58. A system for scanning a light beam over a target, the system comprising:
- a first lens element disposed along a path of the light beam, the first lens element converging the light beam to a waist beyond which the light beam becomes a diverging light beam;
- a second lens element disposed along the path of the diverging light beam, the second lens substantially collimating the light beam to within about 30 milliradians or less for the full width of the beam, the beam waist disposed between the first lens element and the second lens element, and which is also disposed between the first lens element and a focal point of the second lens element; and
- a first movable mirror for scanning the path of the light beam from a first position on the target to a second position on the target, the mirror disposed along the beam path between the first lens element and the second lens element, the path from the second lens element in the first position being substantially parallel to the path from the second lens element in the second position.

59. The system of claim 58, wherein a position of the beam waist is separated from the position of the surface of the mirror.

60. The system of claim 59, wherein a dimension across the surface of the mirror intersecting the beam is greater than about 10% of a width of the beam at the second lens element.

61. The system of claim 59, wherein a full angle of the substantially collimated light beam is less than about 15 milliradians and the path of the beam in the first position on the target is parallel to the path of the beam in the second position on the target to within about 15 milliradians.

* * * * *